(12) United States Patent
Kuwabara et al.

(10) Patent No.: US 7,655,457 B2
(45) Date of Patent: **\*Feb. 2, 2010**

(54) CELL CULTURE VESSEL AND CULTURED CELL

(75) Inventors: Kosuke Kuwabara, Hitachi (JP);
Akihiro Miyauchi, Hitachi (JP);
Masahiko Ogino, Hitachi (JP); Takashi Ando, Hitachi (JP)

(73) Assignee: Hitachi, Ltd., Tokyo (JP)

( * ) Notice: Subject to any disclaimer, the term of this patent is extended or adjusted under 35 U.S.C. 154(b) by 607 days.

This patent is subject to a terminal disclaimer.

(21) Appl. No.: 10/989,910

(22) Filed: Nov. 17, 2004

(65) Prior Publication Data
US 2005/0214935 A1      Sep. 29, 2005

(30) Foreign Application Priority Data
Nov. 17, 2003    (JP) ............................. 2003-386053

(51) Int. Cl.
*C12M 1/14*    (2006.01)
*C12M 3/04*    (2006.01)
*C12M 3/00*    (2006.01)
*C12M 1/00*    (2006.01)

(52) U.S. Cl. ............... 435/299.2; 435/283.1; 435/309.4
(58) Field of Classification Search .... 435/283.1–309.4
See application file for complete search history.

(56) References Cited

U.S. PATENT DOCUMENTS

| | | | | |
|---|---|---|---|---|
| 4,761,378 A | * | 8/1988 | Godsey | .................... 435/288.4 |
| 4,975,377 A | * | 12/1990 | Key | ......................... 435/297.5 |
| 5,084,393 A | * | 1/1992 | Rogalsky | .................. 435/299.2 |
| 5,264,344 A | * | 11/1993 | Sneath | ...................... 435/7.32 |
| 6,852,525 B1 | * | 2/2005 | Cantor | .................... 435/288.3 |
| 7,195,872 B2 | * | 3/2007 | Agrawal et al. | ................. 435/6 |

FOREIGN PATENT DOCUMENTS

| | | |
|---|---|---|
| CN | 85 1 03552 | 10/1986 |
| WO | WO 00/37606 | 6/2000 |

* cited by examiner

*Primary Examiner*—Walter D Griffin
*Assistant Examiner*—Lydia Edwards
(74) *Attorney, Agent, or Firm*—Antonelli, Terry, Stout & Kraus, LLP.

(57) ABSTRACT

It is an object of this invention to provide a cell culture vessel which has a simple and convenient structure, can prevent the injury on the cells at the time of peeling, and accelerates the transportation of nutrients and discharge of waste materials. In order to solve the problem mentioned above, the cell culture vessel of this invention has protrusions having a corresponding diameter not smaller than 10 nm and not greater than 10 μm and a height not smaller than 10 nm and not greater than 1 mm on the surface of the cell culture vessel. The protrusions make the culture fluid permeate into the under part of the cells, accelerate the supply of nutrients and discharge of waste materials, and makes the contact between the cells and the vessel as a point-contact and thereby prevents the cells from the injury which the cells undergo at the time of peeling.

10 Claims, 6 Drawing Sheets

100

101

101

CELL CULTURE VESSEL AND CULTURED CELL

This application claims priority from Japanese Patent Application JP 2003-386053 filed on Nov. 17, 2003, the content of which is hereby incorporated by reference into this application.

BACKGROUND OF THE INVENTION

This invention relates to a cell culture vessel and a cultured cell cultured in said vessel.

In the recent years, the technique of cell culture used for the purpose of medical treatment has progressed, and is actually applied to transplantation of the skin, etc. The application of cell culture is not limited to small quantity of cells and tissues such as the skin, but the progress is being directed toward the auto-transplantation and hetero-transplantation of complicated organs such as cornea, teeth, bones, organs, etc.

For the culture of cells, vessels made of glass or resins, such as Petri dish and the like, are used. For example, a Petri dish such as mentioned below is disclosed. A collagen solution having a prescribed concentration is poured onto a culture vessel by means of a pipette so that the surface of the vessel becomes coated uniformly, and thereafter the coated dish is dried for a period of 15 minutes to 72 hours. Otherwise, a collagen solution having a prescribed concentration is coated onto a stretchable culture base material such as silicone film and polymerized in an incubator at 15-42° C. for 20-120 minutes, after which the stretchable culture base material such as silicone film is left standing under an UV lamp for 15 minutes to 72 hours. After the collagen has been dried, the collagen is again moistened with a phosphate buffer solution, and thereafter the collagen is stretched to an extent of 10-40% and fixed to give a dish for use in cell culture (see JP-A-2002-142751 (Example A)).

Further, as another type of cell culture vessel, the following is disclosed. Thus, the bottom of a culture vessel is coated with a polymer which shows a hydrophilic nature at a temperature and a hydrophobic nature at another temperature, and the polymer is immobilized by UV irradiation or the like, whereby a culture vessel suitable for peeling of cell after the culture can be obtained (cf. JP-A-5-244938 (Example 1)).

According to the first method mentioned above, a cell can be cultured on collagen which has an affinity to the cell. Contrarily, however, the adhesive force between cell and culture vessel is so strong that the cultured cell is difficult to peel off from the vessel. Regarding this adhesive force, there has been a problem that mechanical peeling of the cell brings about a physical injury of the cell, so that when the cell is subjected to a chemical treatment using an enzyme such as trypsin or the like, the membrane protein on the surface of cell is broken and percentage of fixing of cell into tissue, after transplantation, decreases.

According to the second method mentioned above, the problem of peeling can be solved by adjusting the waterphilic nature of the surface of culture vessel and thereby decreasing the adhesiveness of cell surface. If such a measure is taken, however, the state of cell culture vessel surface is limited to that of specified material. In addition, the problem how to prepare an arbitrary surface state well coping with various cells, how to shorten the time period for producing a culture vessel, how to transport the nutrients to the central part of sheet-form cell, how to accelerate the discharging of waste-materials, etc. have been remained unsolved yet.

It is an object of this invention to provide a cell culture vessel which is simple and convenient in structure, capable of preventing the injury to cells at the time of peeling, and able to accelerate the transportation of nutrients and discharging of waste materials.

SUMMARY OF THE INVENTION

In order to solve the problem mentioned above, the first aspect of this invention provides a cell culture vessel characterized in that protrusion groups having a corresponding diameter not smaller than 10 nm and not greater that 10 µm and having a height not smaller than 10 nm and not greater than 1 mm are formed on the bottom surface of a cell culture vessel. Due to such a structure, the culture fluid can penetrate under the cells, and promotes the supply of nutrients necessary for the cells and the discharge of waste materials released from the cells. At the same time, the protrusion groups make the contact between the cells and the vessel a point-contact and thereby prevent the cells from the injury at the time of peeling. Further, it is preferable that the protrusion groups have openings through which the culture fluid can flow, in order to accelerate transportation of nutrients and discharge of the waste materials. In the expression given above, the term "corresponding diameter" was used because the cross section is not always circular but it is sometimes elliptic, polygonal, asymmetric, etc. In this invention, the term "corresponding diameter" is used for the purpose of including all these cases completely. As used in this invention, the diameter of the cross section of the bottom surface of protrusion is taken as "corresponding diameter".

It is necessary in this invention to treat the surface of the cell culture vessel so as to make it hydrophilic in order to penetrate the culture fluid. However, it is sometimes necessary to treat the surface of the vessel so as to make it hydrophobic or to coat the surface of the vessel with metal, protein or the like, according to the kind of the cells to be cultured. For this purpose, this invention provides a cell culture vessel in which only the tips of the protrusion groups formed on a cell culture vessel, to be contacted with the cells, have been subjected to a hydrophobic treatment necessary for cell culture or a coating treatment with metal, protein or the like necessary for cell culture.

In case of requiring a specific shape such as orientation property or the like, of the cultured cell, a part of the bottom surface of the cell culture vessel can sometimes be subjected to a specific treatment such as a treatment making the bottom surface hydrophobic, or the like according to the shape of the cultured cell. This invention provides a cell culture vessel in which the surface of the vessel has selectively been subjected to a treatment necessary for cell culture such as a treatment for making hydrophobic the tips of protrusion groups on the cell culture vessel surface, coating the tips with a metal, coating the tips with a protein, or the like.

By applying this invention, there can be provided a cell culture vessel which is simple and convenient in structure, is prevented from the injury of cells at the time of peeling, and is accelerated with regard to transportation of nutrients and discharge of waste materials. Since such an effect is exhibited because of the shape of the protrusion groups, the process for forming the vessel can be made simple. Further, there is an effect that, since no new drugs and treating apparatuses are introduced, it is unnecessary to consider a new discharging method.

DESCRIPTION OF REFERENCE NUMERALS

Figure 1:
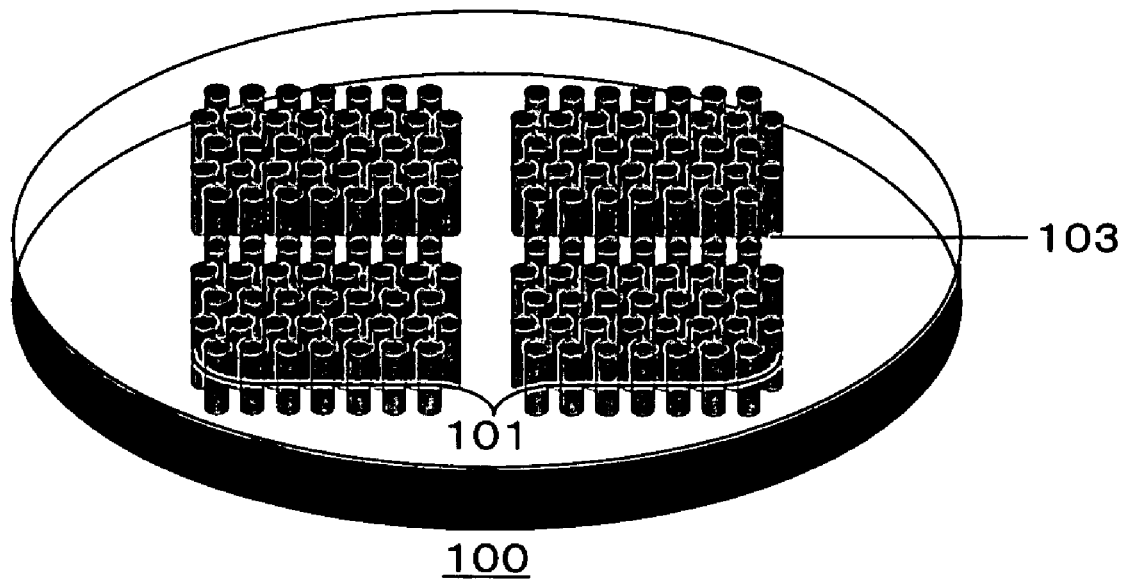
FIG. 1 is a schematic view illustrating one example of the cell culture vessel according to this invention.

100: cell culture vessel, 101: protrusion assembly, 102: surface treatment, 401: vessel, 402: die, 403: shape of the die, 501: surface treatment, 502: stamp, 503: surface treating agent, 701: culture fluid, 702: cell, 801: prismatic minute protrusion groups, 802: underground.

DETAILED DESCRIPTION OF THE INVENTION

Hereunder, the cell culture vessel of this invention will be explained in detail by referring to the drawings.

FIG. 1 is a bird's eye view illustrating the cell culture vessel 100 of this invention. On the bottom surface of vessel 100 containing cells and a culture fluid thereof, a protrusion assembly 101 having a corresponding diameter not smaller than 101 nm and not larger than 10 μm and a height not smaller than 10 nm and not larger than 1 mm are formed. Interstices 103 are formed in the protrusion assembly 101 in order to facilitate the flow of culture fluid.

In FIG. 1, the corresponding diameter of the protrusion assembly 101 is designed so as to become sufficiently smaller than the diameter of the cells, for example, smaller than ⅕ of the cell diameter, in order to decrease the contact area between the protrusion groups and cells. Further, in order to make the culture fluid sufficiently permeate into the under part of the protrusion groups, the height of the protrusion groups is designed so as to become a sufficient height, for example, preferably a height not smaller than the corresponding diameter, and more preferably not smaller than 5 times the corresponding diameter. However, the height preferably does not exceed 100 times the corresponding diameter, from the viewpoint of structural strength.

Figure 2:
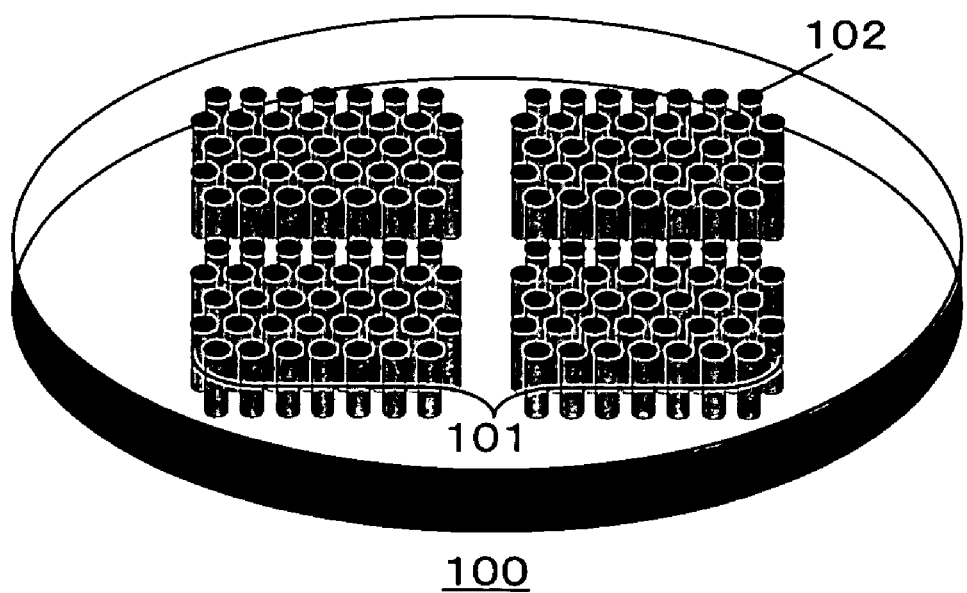
FIG. 2 is a schematic view illustrating another example of the cell culture vessel of this invention.

FIG. 2 is a bird's eye view illustrating the state after carrying out the surface treatment on the tips of protrusion groups of the cell culture vessel 100 of this invention. An assembly of protrusion groups 101 having a corresponding diameter not smaller than 10 nm and not larger than 10 μm and a height not smaller than 10 nm and not greater than 1 mm are formed on the bottom plane of vessel 100 into which cells and cultured fluid are to be introduced, and only the tips of the protrusion groups are subjected to treatment 102 necessary for cell culture, such as hydrophobic treatment, metallic coating, protein coating, etc.

Figure 3:
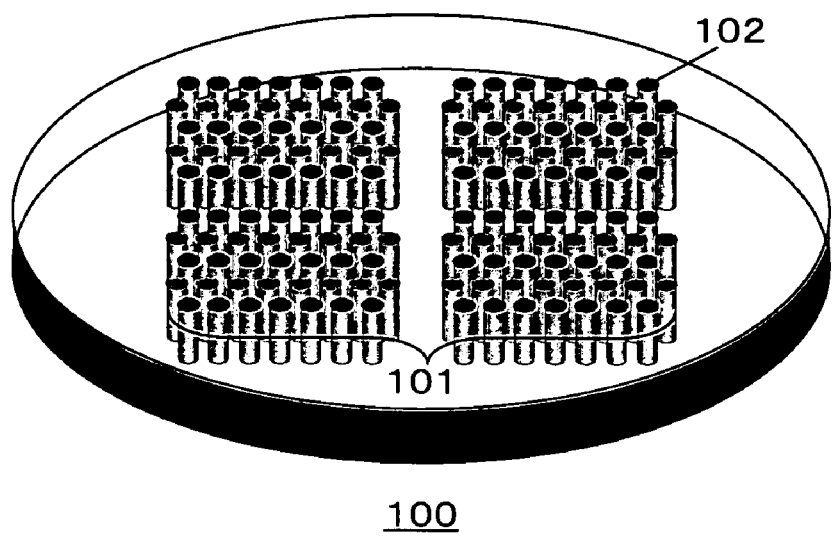
FIG. 3 is a schematic view illustrating a third example of the cell culture vessel of this invention.

FIG. 3 is a bird's eye view illustrating the state after carrying out the surface treatment on a part of the tips of protrusion groups of the cell culture vessel 100 of this invention. An assembly of protrusion groups 101 having a corresponding diameter not smaller than 10 nm and not larger than 10 μm and a height not smaller than 10 nm and not greater than 1 mm are formed on the bottom plane of vessel 100 into which cells and cultured fluid are to be introduced, and a part of the tips of the protrusion groups are subjected to treatment 102 necessary for cell culture, such as hydrophobic treatment, metallic coating, protein coating, etc.

The material constituting the cell culture vessel 100 of this invention is not particularly limited, but the material is selected according to the desired accuracy of processing, surface characteristics, optical characteristics, strength, etc. Concretely saying, thermoplastic resins such as polyethylene, polypropylene, polyvinyl alcohol, polyvinylidene chloride, polyethylene terephthalate, polyvinyl chloride, polystyrene, ABS resin, AS resin, acrylic resin, polyamide, polyacetal, polybutylene terephthalate, glass-reinforced polyethylene terephthalate, polycarbonate, modified polyphenylene ether, polyphenylene sulfide, polyether ether ketone, liquid-crystalline polymer, fluororesins, polyallate, polysulfone, polyether sulfone, polyamide-imide, polyether-imide, thermoplastic polyimide and the like; thermosetting resins such as phenolic resin, melamine resin, urea resin, epoxy resin, unsaturated polyester resin, alkyd resin, silicone resin, diallyl phthalate resin, polyamido-bismaleimide, polybisamido-triazole and the like; and materials prepared by blending two or more kinds of the above-mentioned materials can be used. In addition to above, inorganic materials such as quartz, glasses, and the like can also be used.

The material for constructing the protrusion assembly 101 of this invention is not particularly limited. The above-mentioned resin compositions, or inorganic materials such as quartz, glasses, etc. may be used according to the desired processing accuracy, surface characteristics, optical characteristics, strength, etc. When strength of the protrusion groups has an important meaning, it is preferable that the protrusion groups are made of the same material as used in the cell culture vessel and are integrated therewith.

Figure 4:
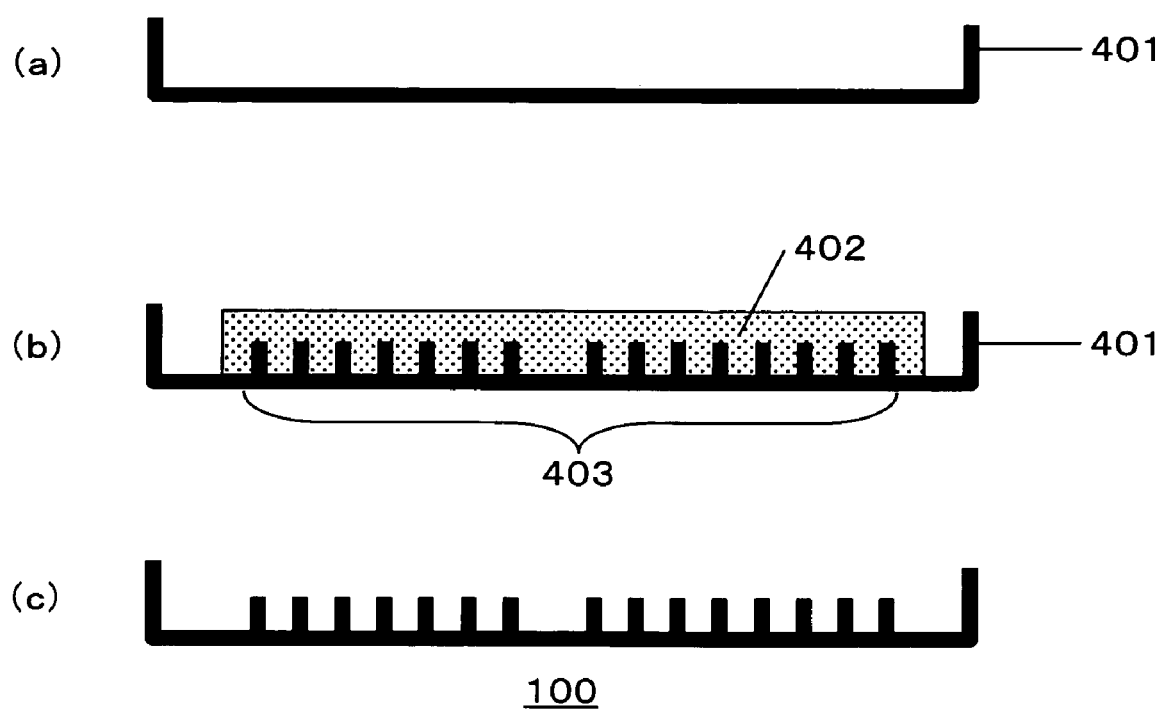
FIG. 4 is a schematic view illustrating the procedure for forming protrusion groups on the surface of cell culture vessel.

FIG. 4 illustrates the procedure for forming protrusion groups on the bottom surface of a cell culture vessel of this invention. Vessel 401 is softened by heating, and die 402 on which minute irregular patterns are formed thereon is pushed against the softened vessel, whereby the minute shape 403 on the die 402 is transferred onto the vessel 401. Thus, a cell culture vessel 100 having protrusion groups formed thereon can be obtained.

The minute shape 403 on the die 402 is required to have a size necessary for making the protrusions on the cell culture vessel 400 have a size necessary for exhibiting the above-mentioned effect, a corresponding diameter not smaller than 10 nm and not greater than 10 μm, and a height not smaller than 10 nm and not greater than 1 mm. Therefore, the die contains, as constructing materials thereof, at least one of metals, inorganic materials such as carbon, silicon and the like, and resin compositions, and the surface shape thereof is formed by a minute processing method such as photo-lithographic method, electron beam direct picturing method, particle beam processing method or scanning probe processing method, or by self-organization of fine particles, or by nano-printing method, injection molding method, non-electrolytic and the like using master formed by the above-mentioned methods. Although the method of pushing a die against a softened vessel or the so-called nanoprinting method is used in FIG. 4 as a method for forming protrusion groups, it is needless to say that other molding methods of resins typified by injection molding method or a direct processing by laser processing or the like, using no die, can also be adopted.

In this invention, according to desire, the cell culture vessel is subjected to a surface treatment necessary for cell culture by immersion in a solution using a solvent containing an oxidant such as hydrogen peroxide, ozone or the like, ultra-violet irradiation, a hydrophilc treatment by gas phase treatment such as plasma treatment, coating with protein by immersion in a solution, or plating, metal coating by vapor deposition method, or surface modification by the use of light, electron beams, particle beams or the like.

Figure 5:
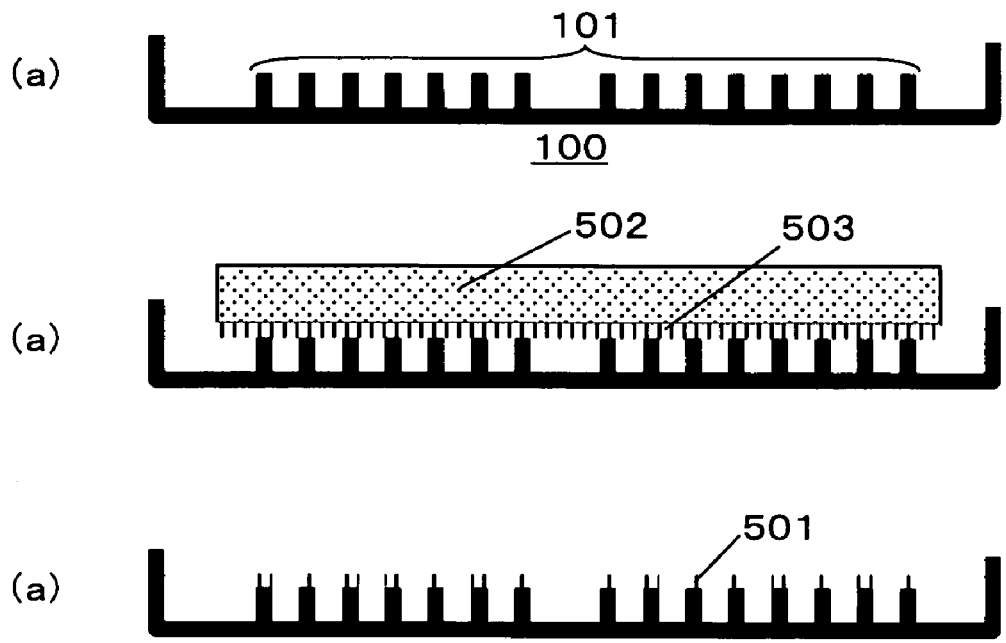
FIG. 5 is a schematic view illustrating the method of surface modification to be carried out only on the tips of the protrusion groups.

Next, the method for modifying the surface only on the tips of protrusions will be explained with reference to FIG. 5. Stamp 502 carrying treating agent 503 adhered to surface thereof is closely contacted against cell culture vessel 100 on which protrusions have been formed and the whole surface thereof has been subjected to the necessary surface treatment, and heating, irradiation with light, etc. applied thereto, if necessary. In this manner, only the tip part of the protrusion assembly 101 contacted with stamp 502 can be subjected to the desired surface treatment 501.

Figure 6:
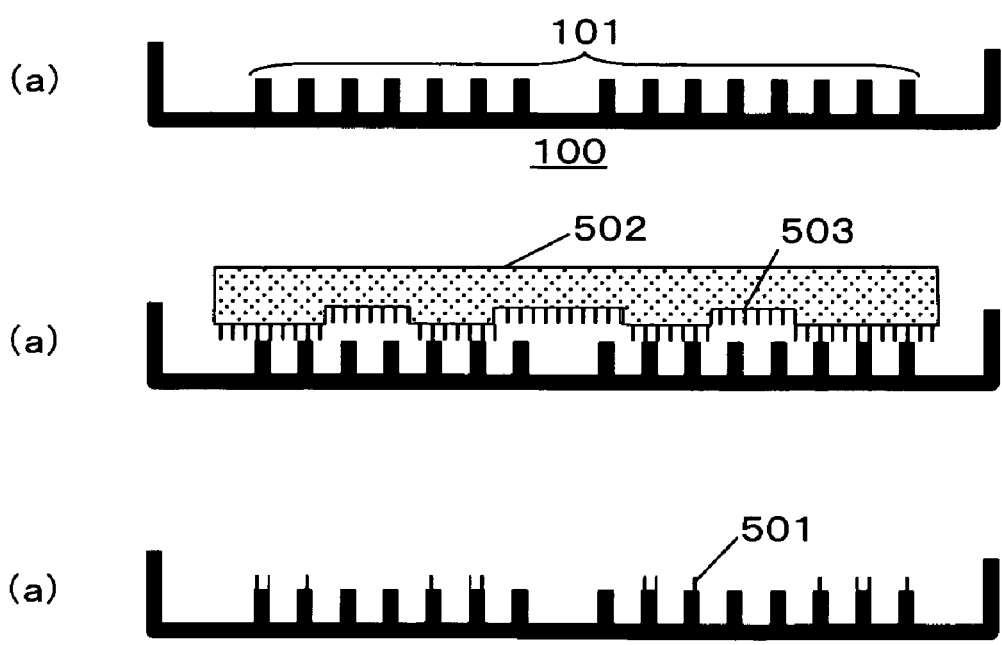
FIG. 6 is a schematic view illustrating the method for modification which forms a distribution of treatments on the tips of the protrusion groups.

It is necessary to make a uniform and even adhesion between stamp 502 and the many protrusion assemblies 101 on the surface of cell culture vessel 100. For this purpose, it is desirable that the stamp 502 is made of an elastic material having a necessary elasticity such as silicone rubber, resin, film, metallic thin film, or the like. Here, it is possible, if desired, to make a distribution of the treatment to the tip parts of protrusions by previously forming unevenness 601 on the stamp 502, as shown in FIG. 6.

As the treating agent 503, hydrophobic agents such as resin paste, silicone grease, fluorine-type coating agent and the like, and protein-containing solvents can be referred to. At the time of applying the treating agent 503 to the stamp 502, it is also possible to form a distribution of the treatment on the tip part of protrusions by realizing an in-plane distribution with regard to presence of treating agent or concentration thereof. Further, when the tip part of protrusion assembly 101 is directly changed by heating or the like, the treating agent 503 may be omitted.

Figure 7:
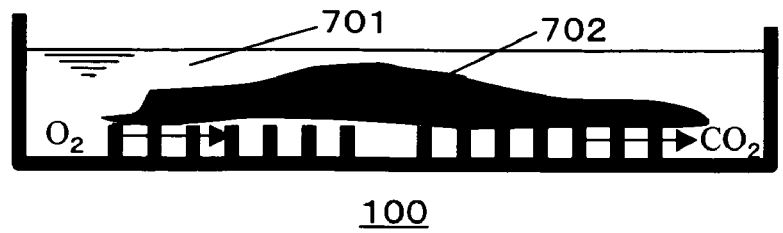
FIG. 7 is a schematic view illustrating the method for using the cell culture vessel of this invention.

FIG. 7 illustrates the method for using the cell culture vessel 100 of this invention. The inner atmosphere of cell culture vessel 100 is filled with culture fluid 701, and cells 702 are provided on the protrusion assembly 101. Thereafter, the cells 702 are cultured in the usual manner. Since the contact between cells 702 and vessel is a point-to-point contact in the cell culture vessel 100 of this invention, the cells 702 can be prevented from the injury at the time of peeling off the cells 702. Further, by changing the shape of protrusion assembly 101 and the surface treatment of protrusion assembly 101 according to the cell 702 to be cultured, cultured cells of high quality can be formed without injury at the time of peeling.

Herein, the word "cultured cell" is a conception involving the cultured cells made into a tissue exemplified by cultured tissue and organs, too.

DESCRIPTION OF PREFERRED EMBODIMENTS

Hereunder, this invention is further explained in detail by referring to examples.

Example 1

Figure 8:
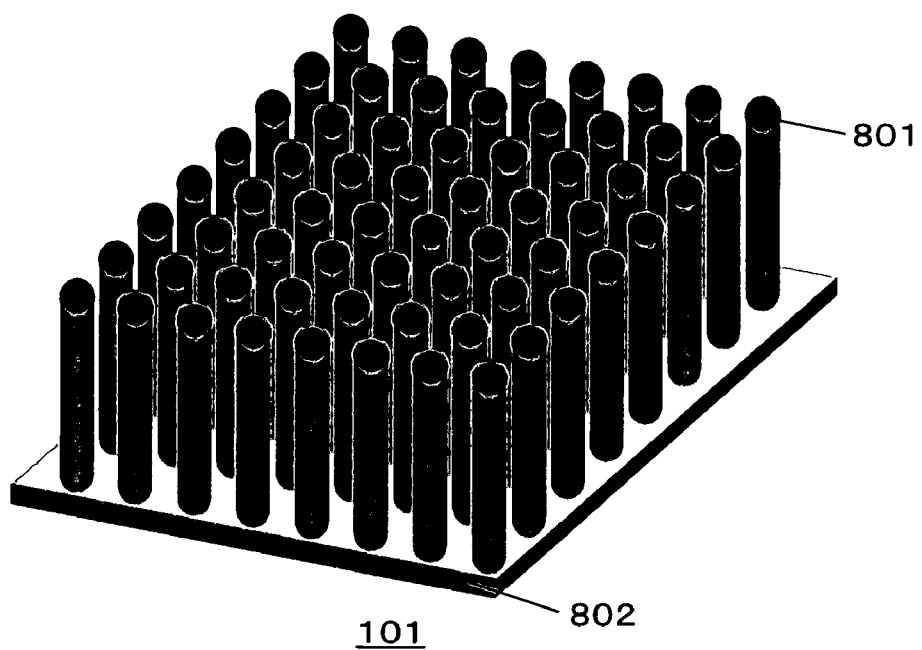
FIG. 8 is a schematic view illustrating the scanning electron microscopic photograph of the protrusion assembly prepared in Example 1.

One example of this invention is explained below. FIG. 8 is a schematic view illustrating a scanning electron microscopic photograph of protrusion assembly 101 prepared according to this example. The protrusion assembly 101 consists of a plurality of prismatic minute protrusions 801. The material constituting the prismatic minute protrusions 801 is polystyrene having a molecular weight of 2,000 to 600,000. The upper limit of the molecular weight can be further extended to 6,000,000.

Figure 9:
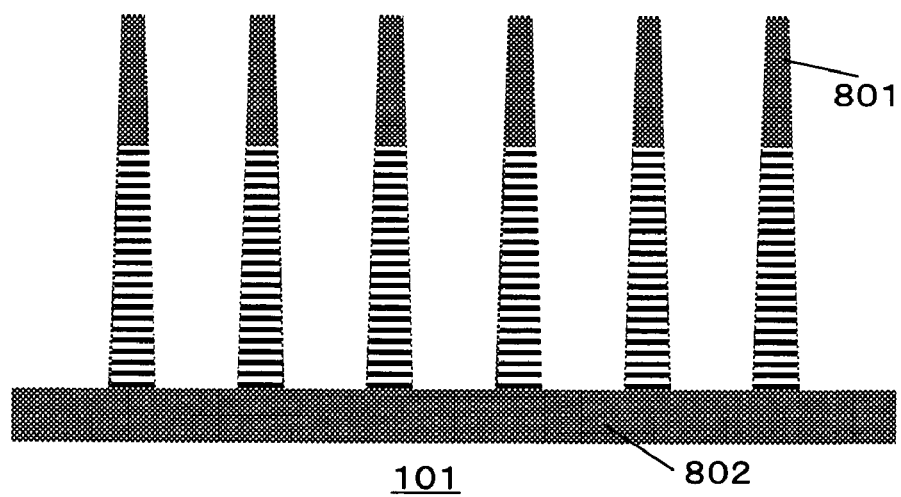
FIG. 9 is a schematic view illustrating an expanded scanning electron microscopic photograph of the protrusion assembly.

FIG. 9 is a schematic view of an expanded scanning electron microscopic photograph of the protrusion assembly 101. The height of the prismatic minute protrusion 801 is 3 μm, and the length of one side thereof is 300 nm as measured at the root. The upper part, about 1 μm in length, of the prismatic minute protrusion 801 has a flat and smooth surface, while its lower part, up to the position of about 2 μm from the root, has a stripe pattern.

Since one side of the bottom plane of the prismatic minute protrusion 801 has a length of 300 nm and a height of 3 μm, the height to one side ratio is 10, which is greater than 1.

It is also seen that the prismatic minute protrusion 801 is smaller in the tip part than in the bottom part, or it has a spread-out shape like an unfolded fan. In this example, the prismatic minute protrusion 801 is so shaped that its thickness becomes gradually thinner from the root to the tip. However, it is possible that it has a mushroom-like shape in which the thickness gradually becomes thinner from the root to the upper part and the thickness rapidly increases in the tip part. One of the characteristic features of the prismatic minute protrusion 801 of this invention is that there exists a part of becoming slender from the root to the tip.

Further, the prismatic minute protrusion 801 is made of the same polystyrene as in the underground part 802.

Further, the prismatic minute protrusion 801 is connected to the underground 802 and integrated therewith.

Further, since the tip part of the protrusion is smaller than the bottom part or it has a spread-out shape like an unfolded fan, there is an effect that the protrusions are not readily taken out of the base board. Further, since the protrusions are made of the same material as in the underground, there is an effect that the protrusions are not readily taken out of the underground. Further, since the protrusions are integrated with the base board, there is an effect that the protrusions are not readily taken out of the base board.

Although in this example polystyrene was used as material for constituting the prismatic minute protrusion 801 and bottom plane 802, it is also possible to use the materials presented in the description given above as the material for constituting the cell culture vessel.

Figure 10:
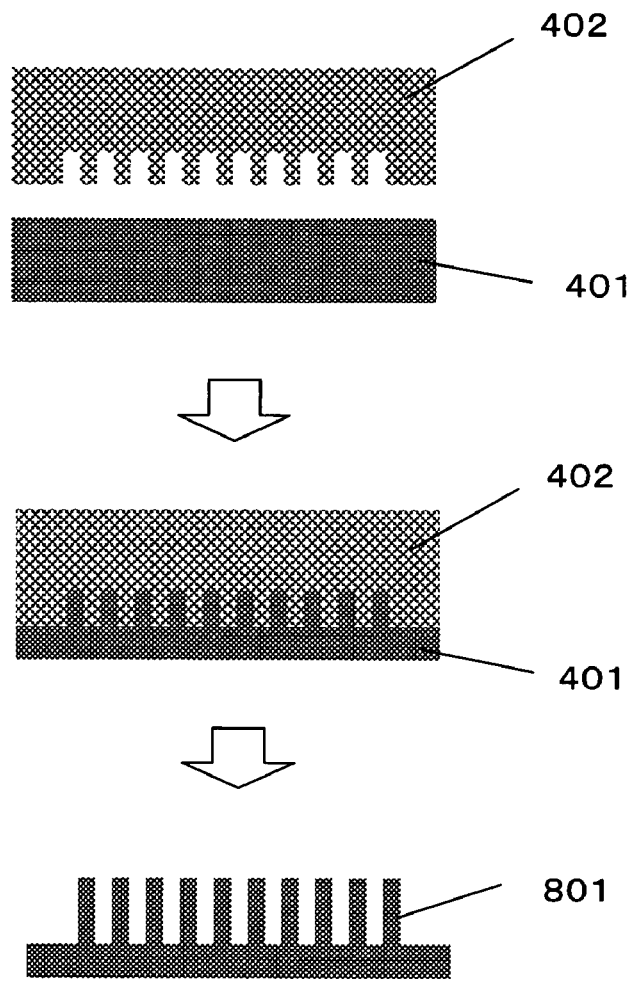
FIG. 10 is a schematic view illustrating the process for producing the prismatic minute protrusion groups.

The above-mentioned prismatic minute protrusion 801 was prepared in the following manner. FIG. 10 is the process for preparing the prismatic minute protrusion 801. Vessel 401 was heated to 100° C., and a die 402 on the whole surface of which minute holes having a diameter of 0.5 μm and a depth of 1.0 μm were formed at a pitch of 1.0 μm was pressed against vessel 401 under a press pressure of 4 MPa for a period of 300 s. After cooling the vessel to 70° C. in the press, die 402 and vessel 401 were taken out of the press, and die 402 was peeled off from vessel 401 by perpendicularly drawing up die 402 from vessel 401 to obtain a cell culture vessel 100 having prismatic minute protrusions 801. The die 402 was a silicon wafer having a crystal dimension of (100) and a diameter of 25 mm. The aspect ratio of the prismatic minute protrusions 801 subjected to a demolding treatment with a fluorine type demolding agent for preventing adhesion to vessel 401 at the time of molding is about 3 times as great as the aspect ratio of the unevenness of die 402. Although a structure of such a high aspect ratio can be formed on the cell culture vessel 100 by forming unevenness of large aspect ratio on die 402, prismatic minute protrusion 801 of high aspect ratio can be formed from a die 402 having a low aspect ratio which is relatively easy to form, by the use of the procedure of this example.

In this example, polystyrene was used as a material of vessel 401. However, the material constituting vessel 401 is not limited to polystyrene, but organic materials such as polycarbonate and the like, inorganic materials such as glass and the like, and laminated structures thereof are also usable.

In this example, a silicon wafer having a crystal dimension of (100) and a diameter of 25 mm was used as the die 402. However, it is not particularly necessary that the crystal dimension is (100) or the material constituting the die is single crystal silicone, but it is also possible that the material is a metallic thin film such as nickel or the like or an organic material such as PDMS (polydimethylsiloxane) or the like. In order to prevent the injury of vessel 401 and prismatic minute protrusions 801 at the time of demolding the die 402 from the heated vessel 401, the die 402 is preferably coated with a demolding agent of fluorine type or silicone type.

Further, it is also possible to control the diameter and height of the prismatic minute protrusion 801 by changing the depth of the concave part of die 402 or the material constituting vessel 401.

Further, it is also possible to control the size of the bottom part of prismatic minute protrusion 801 by enlarging the opening area of the concave part of die 402.

Further, the position at which the prismatic minute protrusion 801 is formed can be controlled by changing the concave part of die 402.

Further, it is doubtless that an effect that the shape of prismatic minute protrusion can easily be changed can be obtained by making thermoplastic the material constituting the prismatic minute protrusion and thereby controlling the temperature at the time of forming the prismatic minute protrusion 801.

Further, it is doubtless that an effect of easily controlling the shape of prismatic minute protrusion 801 can be obtained by making photo-curable the material constituting the prismatic minute protrusion 801 and projecting light at the time of forming the prismatic minute protrusion 801.

Example 2

Next, another example of this invention will be explained below. FIG. 1 is a bird's eye view illustrating a cell culture vessel 100 prepared according to the present example. The cell culture vessel 100 is made mainly of polystyrene has a dish-like shape having a thickness of 2 mm and a diameter of 35 mm. On the bottom plane of the cell culture vessel 100 is formed protrusion assembly 101 over a region having a diameter of 30 mm, according to the procedure mentioned in Example 1. After formation of protrusion assembly 101, an oxygen-plasma treatment (100 W, 30 s) was carried out as a hydrophilic treatment. This treatment comprised tightly contacting, to the tip part of the protrusion assembly 101, a surface-hydrophilic PDMS-made flat and smooth stamp of which surface had been coated with a 50 μg/mL collagen solution (Cultrex R Bovine Collagen I, solvent: 0.02M aqueous solution of acetic acid) so that the thickness of the coating was smaller than the height of protrusion assembly 101, to make adhere the collagen I solution only to tip part of the protrusion assembly 101. After removing the stamp, the remainder was kept at room temperature for one hour and washed with PBS (phosphate buffer). Thus, only the tip part of protrusion assembly 101 was modified by collagen, and subjected to surface treatment suitable for cell culture.

In this example, polystyrene was used as a material of cell culture vessel 100. However, the material is not limited to polystyrene, but organic materials such as polycarbonate, inorganic materials such as glass, and laminated structures thereof may also be used. In this example, the size of cell culture vessel 100 was 35 mm in diameter and the diameter of protrusion assembly-forming region had a diameter of 30 mm. However, these values may be varied in accordance with the size of cell to be cultured. The protrusion assemblies 101 are preferably provided so as to have gaps 103. In this example, cross-wise gaps 103 are provided as shown in FIG. 1. The formation of gaps 103 makes easy the flow of cultured fluid and an efficient supply of nutrients to the cells. Further, discharge of waste materials from the cells can be made effective thereby.

In this example, modification with collagen (a kind of protein) was carried out after formation of protrusion assembly 101. However, the method is not limited thereto, a variety of surface treatments such as oxygen-plasma treatment (for example, 100 W, 30 s), ultraviolet irradiation, hydrophilic treatment such as immersion in aqueous solution of ozone or hydrogen peroxide, introduction of functional groups such as amino group, carboxyl group, methyl group, $CF_3$ group, etc. may be carried out appropriately in accordance with the kind of cell to be cultured and the materials constituting the cell culture vessel 100 and protrusion assembly 101. Further, it is also possible to carry out the surface treatment only on a part of the protrusion assembly 101 by the method shown in FIGS. 5 and 6.

Example 3

Hereunder, an example of culturing cells by the use of the cell culture vessel 100 of this invention will be mentioned. FIG. 7 is a schematic view of culturing cells by the use of cell culture vessel 100 prepared according to the present example 2.

A cultured fluid was introduced into cell culture vessel 100. In the cell culture vessel 100, normal human cuticle keratinized cells were cultured (medium: HuMedia-KB2, manufactured by Kurabou K.K, 37° C., under 5% $CO_2$). As a result, the cuticle keratinized cells deposited normally, and grown up into a form of a sheet.

Fourteen days after the start of the culture, the cultured cells were covered with a polyvinylidene difluoride (PVDF) film and the medium was sucked out, whereby the cuticle keratinized cells could be peeled off from the cell culture vessel 100 together with the PVDF film. The injury on the sheet-form cuticle keratinized cells caused by the peeling-off from the cell culture vessel 100 could be much lightened as compared with that in the case of using a glass-made dish.

Example 4

Hereunder, a case that cells were cultured by the use of the cell culture vessel of this invention and the peeling characteristics of cells were greatly improved will be mentioned.

Figure 11:
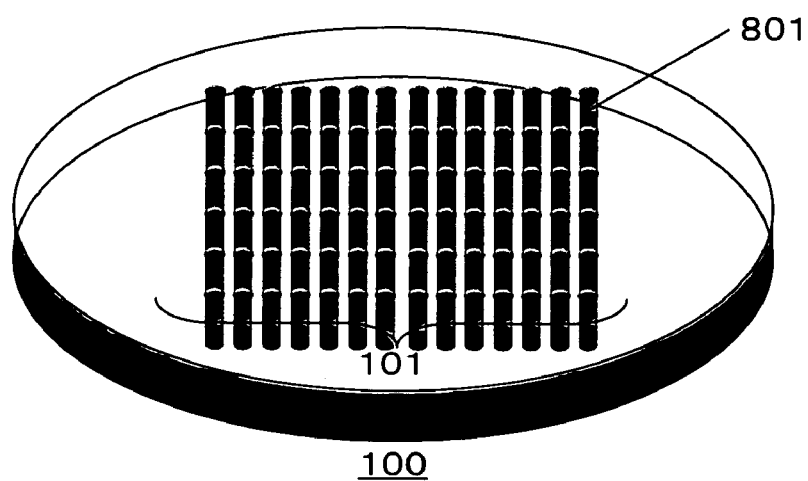
FIG. 11 is a schematic view illustrating one example of the cell culture vessel prepared in Example 4.
Figure 12:
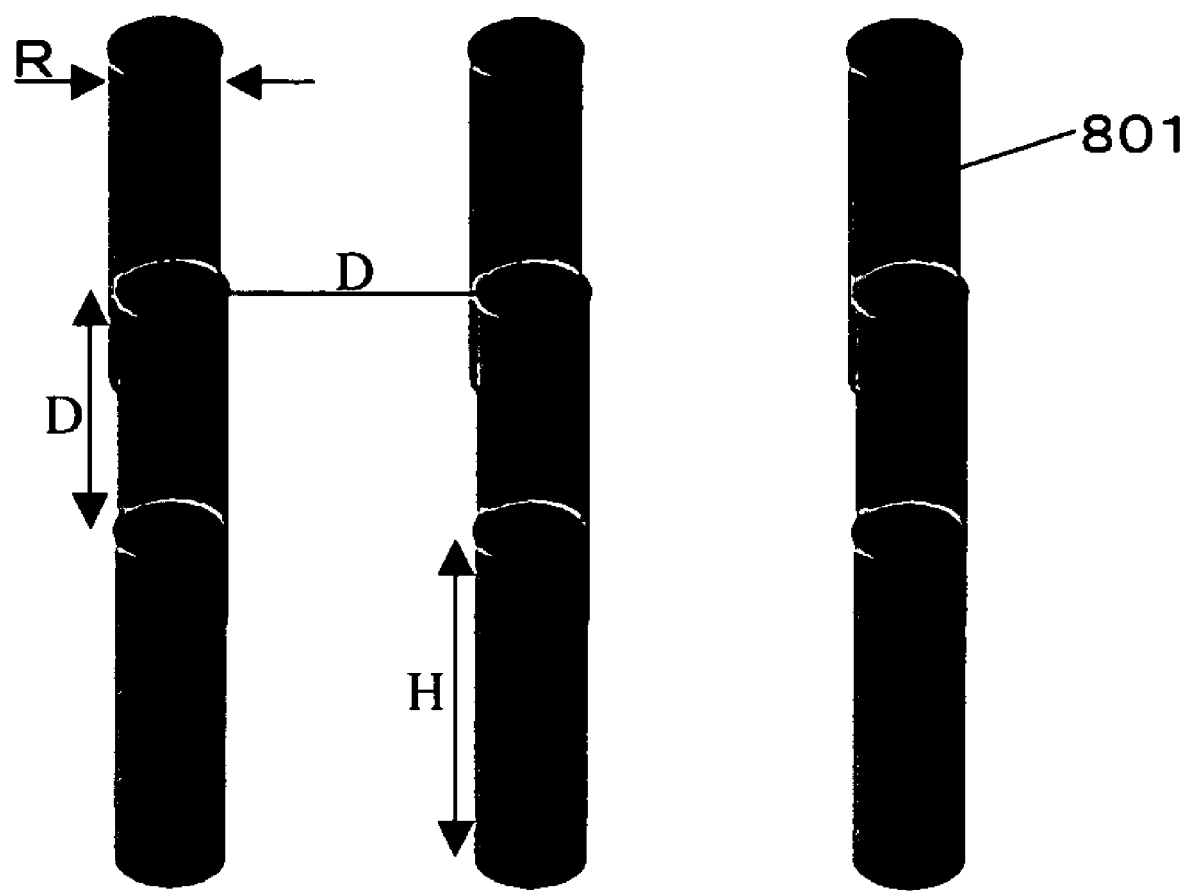
FIG. 12 is a schematic view illustrating the expanded view of the prismatic minute protrusion groups on the cell culture vessel prepared in Example 4.

FIG. 11 is an example of the shape of cell culture vessel 100 prepared in the present example according to the procedure mentioned in Example 1. FIG. 12 is an expanded view of the prismatic minute protrusion 801 constituting the protrusion assembly 101 on the cell culture vessel 100. In this example, in order to investigate the relationship between peeling characteristics of the cultured cell and the shape of prismatic minute protrusion 801 constituting the protrusion assembly 101, four cell culture vessels 100 were prepared in which diameter R of prismatic minute protrusion 801 was 180 nm, 240 nm, 500 nm and 2 μm. In all of the four cell culture vessel 100, the height H of prismatic minute protrusion was 3 μm. The arrangement of prismatic minute protrusions 801 was 2-dimensional regular square lattice as shown in FIGS. 11 and 12, the distance D between the neighboring prismatic minute protrusions 801 was twice the diameter R.

In order to evaluate the peeling characteristics, on each of the cell culture vessel 100, human mesenchyme stem cells (Cyro hMSC, No. 2051, manufactured by CAMBREX Co.) were seeded in a medium (a medium for growing mesenchyme stem cells) and cultured at 37° C. for 5 days under 5% $CO_2$ in an incubator. For comparison, human mesenchyme stem cells were cultured under the same conditions as above in the generally used animal cell culture dish (Corning Co.).

Peeling characteristics were evaluated by observing whether or not human mesenchyme stem cells on a cell culture vessel 100 were peeled off by a water stream generated in the medium after a culture continued for five days. The water stream was generated by discharging the culture fluid used for the culture at an angle of 70 degrees against the bottom plane from the neighborhood of the bottom plane of the cell culture vessel 100, by means of a pipette chip having a capacity of 200 μl equipped with a 250 μl electromotive pipette (EDP plus EP-250).

Table 1 illustrates the result of microscopically observing the peeling of cells on the cell culture vessel 100 caused by one discharging of the medium. In any of the cell culture vessels 100 formed according to this invention, peeling characteristic of the human mesenchyme stem cell was improved as compared with the results in the animal cell culture dishes used for comparison. The peeling characteristic of the human mesenchyme stem cell from the cell culture vessel 100 was dependent on diameter R of the prismatic minutes protrusion 801, and the greatest peeling ability was given when the diameter was as large as R=2 μm. This indicates that the adhesive force of the human mesenchyme stem cell which is an adhesive cell becomes small on the prismatic minutes protrusion 801, and shows an excellent peeling characteristic.

TABLE 1

| Amount of discharge (μl) | Velocity of discharge (μl/sec) | Example A R = 180 nm | Example B R = 240 nm | Example C R = 500 nm | Example D R = 2 μm | Comparative Example Animal cell culture dish |
|---|---|---|---|---|---|---|
| 50 | 56 | − | − | − | − | − |
|  | 112 | − | ± | ± | + | − |
|  | 192 | + | + | + | + | − |
| 100 | 56 | − | − | − | − | − |
|  | 112 | ± | ± | + | ++ | − |
|  | 192 | ++ | ++ | ++ | ++ | − |
| 200 | 56 | − | − | − | − | − |
|  | 112 | ± | + | + | ++ | − |
|  | 192 | ++ | ++ | ++ | +++ | − |

+++: Quite readily peeled off
++: Readily peeled off
+: Peeled off
±: Slightly peeled off
−: Not peeled off at all Although the description presented above was with reference to examples. However, this invention is not limited by the examples, but it is apparent to the specialists in the art that a variety of alteration and modification can be made so far as the essentiality of this invention and the scope of the accompanying claim are not exceeded.

The invention claimed is:

1. A cell culture vessel comprising:
   protrusions having a corresponding diameter not smaller than 10 nm and not greater than 10 μm; and
   a height not smaller than 10 nm and not greater than 1 mm, wherein said protrusions are formed on the bottom plane of the cell culture vessel,
   wherein corresponding diameter of the protrusions formed on the bottom plane of the cell culture vessel is smaller than the diameter of the cell cultured in said cell culture vessel, and
   wherein the corresponding diameter of the protrusions formed on the bottom plane of the cell culture vessel is not greater than one fifth of the diameter of the cell cultured in said cell culture vessel.

2. A cell culture vessel according to claim 1, wherein the protrusions formed on the bottom plane of the cell culture vessel are separated from each other by a predetermined distance that is smaller than the diameter of the cells cultured in said cell culture vessel.

3. A cell culture vessel according to claim 1, wherein the cell culture vessel and the protrusions are made of the same material and integrated.

4. A cell culture vessel according to claim 1, wherein the whole or a part of the cell culture vessel is subjected to at least one treatment selected from the group consisting of hydrophilic treatment, hydrophobic treatment, formation of a metal layer, and coating with an organic material.

5. A cell culture vessel according to claim 1, wherein a specified region is selectively subjected to at least one treatment selected from the group consisting of hydrophilic treatment, hydrophobic treatment, formation of a metal layer, and coating with an organic material.

6. A cell culture vessel according to claim 1, wherein each of the individual protrusions is selectively subjected to at least one treatment selected from the group consisting of hydrophilic treatment, hydrophobic treatment, formation of a metal layer, and coating with an organic material.

7. A cell culture vessel according to claim 1, wherein only tip parts of the protrusions are subjected to hydrophilic treatment, hydrophobic treatment, formation of a metal layer or coating with an organic material.

8. A cell culture vessel according to claim 1, wherein the protrusions have a row-wise opening region through which a liquid material can be passed on the surface of the cell culture vessel.

9. A cell culture vessel comprising:
a vessel for containing a culture fluid; and
protrusions formed on the bottom plane of said vessel, wherein said vessel and said protrusions are made of an identical material,
wherein the corresponding diameter of the protrusions formed on the bottom plane of the cell culture vessel is smaller than the diameter of the cell cultured in said cell culture vessel, and
wherein the protrusions formed on the bottom plane of the cell culture vessel are separated from each other by a predetermined distance that is smaller than the diameter of the cell cultured in said cell culture vessel.

10. A cell culture vessel according to claim 9, wherein the corresponding diameter of the protrusions formed on the bottom plane of the cell culture vessel is not greater than one fifth of the diameter of the cell cultured in the cell culture vessel.

* * * * *